(12) United States Patent
Haap et al.

(10) Patent No.: US 7,015,228 B2
(45) Date of Patent: Mar. 21, 2006

(54) 4-AMINO-2-(2-PYRIDYL)PYRIMIDINES AS MICROBICIDAL ACTIVE SUBSTANCES

(75) Inventors: Wolfgang Haap, Grenzach-Wyhlen (DE); Werner Hölzl, Eschentzwiller (FR); Karin Petzold, Fischingen (DE)

(73) Assignee: Ciba Specialty Chemicals Corporation, Tarrytown, NY (US)

(*) Notice: Subject to any disclaimer, the term of this patent is extended or adjusted under 35 U.S.C. 154(b) by 0 days.

(21) Appl. No.: 10/124,198

(22) Filed: Apr. 17, 2002

(65) Prior Publication Data

US 2003/0092718 A1 May 15, 2003

(30) Foreign Application Priority Data

Apr. 20, 2001 (EP) ................................ 01810387

(51) Int. Cl.
*A61K 31/506* (2006.01)
*A61P 31/00* (2006.01)
*A61P 31/04* (2006.01)
*C07D 239/42* (2006.01)

(52) U.S. Cl. ..................... 514/256; 514/272; 514/273; 544/320; 544/328

(58) Field of Classification Search ................ 514/256, 514/272, 273; 544/328, 320

See application file for complete search history.

(56) References Cited

U.S. PATENT DOCUMENTS

| | | | | |
|---|---|---|---|---|
| 5,250,530 | A | * 10/1993 | Giencke et al. | 514/256 |
| 5,346,899 | A | 9/1994 | Mueller et al. | 514/256 |
| 2002/0168761 | A1 | * 11/2002 | Gour et al. | 435/325 |
| 2003/0069239 | A1 | * 4/2003 | Cai et al. | 514/235.8 |

FOREIGN PATENT DOCUMENTS

| | | | |
|---|---|---|---|
| DE | 4029649 | | 3/1992 |
| DE | 19836697 A1 | * | 2/2000 |
| WO | 00/09496 | * | 2/2000 |
| WO | 01/53331 | * | 7/2001 |

* cited by examiner

Primary Examiner—Venkataraman Balasubramanian
(74) Attorney, Agent, or Firm—Joseph C. Suhadolnik

(57) ABSTRACT

Compounds of formula

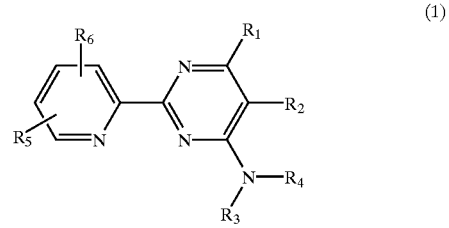

(1)

wherein
$R_1$ and $R_2$ are each independently of the other hydrogen; unsubstituted or mono- or poly-halo-substituted $C_1$–$C_{20}$alkyl, $C_1$–$C_{20}$alkoxy, $C_2$–$C_{20}$alkenyl, $C_2$–$C_{20}$alkynyl, $C_3$–$C_{18}$cycloalkyl, $C_3$–$C_7$cycloalkyl-$C_1$–$C_{20}$alkyl; hydroxy; $C_1$–$C_6$alkoxy-$C_1$–$C_{20}$alkyl; carboxy; $C_1$–$C_6$alkyloxycarbonyl; cyano; mono- or di-$C_1$–$C_{20}$alkylamino; $C_1$–$C_6$alkylamino-$C_1$–$C_{20}$alkyl; halogen; phenyl; unsubstituted or $C_1$–$C_5$alkyl-, halo- or hydroxy-substituted phenyl-$C_1$–$C_{20}$alkyl, phenoxy or phenyl-$C_1$–$C_{20}$alkoxy; or $R_1$ and $R_2$ form a polymethylene chain of formula —$(CH_2)_m$— wherein m=2–12;
$R_3$ is unsubstituted $C_7$–$C_{20}$alkyl; or amino-, hydroxy-, carboxy- or $C_1$–$C_6$alkyloxycarbonyl-substituted $C_2$–$C_{20}$alkyl; $C_8$–$C_{18}$cycloalkyl; $C_8$–$C_{20}$alkenyl; $C_8$–$C_{20}$alkynyl; $C_3$–$C_7$cycloalkyl-$C_8$–$C_{20}$alkyl; $C_1$–$C_4$alkoxy-$C_8$–$C_{20}$alkyl; $R_7R_8N$—$C_7$–$C_{20}$alkyl; phenyl; phenyl-$C_1$–$C_4$alkyl; or phenyl-$C_1$–$C_4$alkoxy;
$R_4$ is hydrogen; unsubstituted or $C_1$–$C_5$alkyl-, halo- or hydroxy-substituted $C_1$–$C_{20}$alkyl, $C_2$–$C_{20}$alkenyl, $C_2$–$C_{20}$alkynyl, $C_3$–$C_{20}$cycloalkyl, $C_3$–$C_7$cycloalkyl-$C_1$–$C_{20}$alkyl, $C_1$–$C_{20}$alkoxy-$C_1$–$C_6$alkyl or $R_7R_8N$—$C_1$–$C_{20}$alkyl, phenyl, phenyl-$C_1$–$C_{20}$alkyl or phenoxy-$C_1$–$C_{20}$alkyl;
$R_5$ and $R_6$ are each independently of the other hydrogen; $C_1$–$C_{20}$alkyl; $C_2$–$C_{20}$alkenyl; $C_2$–$C_{20}$-alkynyl; $C_3$–$C_{18}$cycloalkyl; $C_3$–$C_7$cycloalkyl-$C_1$–$C_{20}$alkyl; hydroxy; $C_2$–$C_{20}$alkoxy; $C_1$–$C_6$alkoxy-$C_1$–$C_{20}$alkyl; carboxy; $C_1$–$C_6$alkyloxycarbonyl; cyano; nitro; $C_1$–$C_{20}$alkylamino; $C_1$–$C_{20}$alkylaminoalkyl; $C_1$–$C_{20}$haloalkyl; $C_1$–$C_{20}$haloalkoxy; halogen; unsubstituted or $C_1$–$C_5$alkyl-, halo- or hydroxy-substituted phenyl, phenoxy or phenyl-$C_1$–$C_{20}$alkyl or phenyl-$C_1$–$C_{20}$alkoxy; or $R_5$ and $R_6$ together form a polymethylene chain of formula —$(CH_2)_m$— wherein m=2–12; and
$R_7$ and $R_8$ are each independently of the other hydrogen; $C_1$–$C_{20}$alkyl; $C_3$–$C_{20}$alkenyl; $C_3$–$C_{20}$alkynyl; $C_3$–$C_7$cycloalkyl; $C_3$–$C_{20}$cycloalkyl-$C_1$–$C_4$alkyl; phenyl; or phenyl-$C_1$–$C_4$alkyl are suitable for the antimicrobial treatment of surfaces.

10 Claims, No Drawings

4-AMINO-2-(2-PYRIDYL)PYRIMIDINES AS MICROBICIDAL ACTIVE SUBSTANCES

The present invention relates to substituted 4-amino-2-(2-pyridyl)pyrimidines, to the preparation of such compounds, and to their use for the antimicrobial treatment of surfaces, as antimicrobial active substances against gram-positive and gram-negative bacteria, yeasts and fungi and also in the preservation of cosmetics, household products, textiles and plastics and for use in disinfectants.

The substituted 4-amino-2-(2-pyridyl)pyrimidines according to the invention correspond to formula

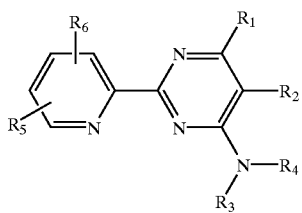

(1)

wherein $R_1$ and $R_2$ are each independently of the other hydrogen; unsubstituted or mono- or poly-halo-substituted $C_1$–$C_{20}$alkyl, $C_1$–$C_{20}$alkoxy, $C_2$–$C_{20}$alkenyl, $C_2$–$C_{20}$alkynyl, $C_3$–$C_{18}$cycloalkyl, $C_3$–$C_7$cycloalkyl-$C_1$–$C_{20}$alkyl; hydroxy; $C_1$–$C_6$alkoxy-$C_1$–$C_{20}$alkyl; carboxy; $C_1$–$C_6$alkyl-oxycarbonyl; cyano; mono- or di-$C_1$–$C_{20}$alkylamino; $C_1$–$C_6$alkylamino-$C_1$–$C_{20}$alkyl; halogen; phenyl; unsubstituted or $C_1$–$C_5$alkyl-, halo- or hydroxy-substituted phenyl-$C_1$–$C_{20}$alkyl, phenoxy or phenyl-$C_1$–$C_{20}$alkoxy; or $R_1$ and $R_2$ form a polymethylene chain of formula —$(CH_2)_m$— wherein m=2–12;

$R_3$ is unsubstituted $C_7$–$C_{20}$alkyl; or amino-, hydroxy-, carboxy- or $C_1$–$C_6$alkyloxycarbonyl-substituted $C_2$–$C_{20}$alkyl, $C_8$–$C_{18}$cycloalkyl, $C_8$–$C_{20}$alkenyl, $C_8$–$C_{20}$alkynyl, $C_3$–$C_7$cycloalkyl-$C_8$–$C_{20}$alkyl, $C_1$–$C_4$alkoxy-$C_8$–$C_{20}$alkyl, $R_7R_8N$—$C_7$–$C_{20}$alkyl, phenyl, phenyl-$C_1$–$C_4$alkyl or phenyl-$C_1$–$C_4$alkoxy;

$R_4$ is hydrogen; unsubstituted or $C_1$–$C_5$alkyl-, halo- or hydroxy-substituted $C_1$–$C_{20}$alkyl, $C_2$–$C_{20}$alkenyl, $C_2$–$C_{20}$alkynyl, $C_3$–$C_{20}$cycloalkyl, $C_3$–$C_7$cycloalkyl-$C_1$–$C_{20}$alkyl, $C_1$–$C_{20}$alkoxy-$C_1$–$C_6$alkyl or $R_7R_8N$—$C_1$–$C_{20}$alkyl, phenyl, phenyl-$C_1$–$C_{20}$alkyl or phenoxy-$C_1$–$C_{20}$alkyl;

$R_5$ and $R_6$ are each independently of the other hydrogen; $C_1$–$C_{20}$alkyl; $C_2$–$C_{20}$alkenyl; $C_2$–$C_{20}$-alkynyl; $C_3$–$C_{18}$cycloalkyl; $C_3$–$C_7$cycloalkyl-$C_1$–$C_{20}$alkyl; hydroxy; $C_2$–$C_{20}$alkoxy; $C_1$–$C_6$alkoxy-$C_1$–$C_{20}$alkyl; carboxy; $C_1$–$C_6$alkyloxycarbonyl; cyano; nitro; $C_1$–$C_{20}$alkylamino; $C_1$–$C_{20}$alkylaminoalkyl; $C_1$–$C_{20}$haloalkyl; $C_1$–$C_{20}$haloalkoxy; halogen; unsubstituted or $C_1$–$C_5$alkyl-, halo- or hydroxy-substituted phenyl, phenoxy or phenyl-$C_1$–$C_{20}$alkyl or phenyl-$C_1$–$C_{20}$alkoxy; or $R_5$ and $R_6$ together form a polymethylene chain of formula —$(CH_2)_m$— wherein m=2–12; and $R_7$ and $R_8$ are each independently of the other hydrogen; $C_1$–$C_{20}$alkyl; $C_3$–$C_{20}$alkenyl; $C_3$–$C_{20}$-alkynyl; $C_3$–$C_7$cycloalkyl; $C_3$–$C_{20}$cycloalkyl-$C_1$–$C_4$alkyl; phenyl; or phenyl-$C_1$–$C_4$alkyl.

$C_1$–$C_{20}$Alkyl radicals are straight-chain or branched alkyl radicals, for example methyl, ethyl, n-propyl, isopropyl, n-butyl, sec-butyl, tert-butyl, amyl, isoamyl or tert-amyl, heptyl, octyl, isooctyl, nonyl, decyl, undecyl, dodecyl, tetradecyl, pentadecyl, hexadecyl, heptadecyl, octadecyl or eicosyl.

$C_3$–$C_{18}$Cycloalkyl denotes, for example, cyclopropyl, cyclobutyl, cyclopentyl, cycloheptyl, cyclooctyl, cyclononyl, cyclodecyl, cycloundecyl, cyclododecyl, cyclotetradecyl, cyclopentadecyl, cyclohexadecyl, cycloheptadecyl, cyclooctadecyl or, especially, cyclohexyl.

Alkenyl includes, within the scope of the meanings given, inter alia, allyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl and n-octadec-4-enyl.

$C_1$–$C_5$Alkoxy radicals are straight-chain or branched radicals, for example methoxy, ethoxy, propoxy, butoxy or pentyloxy.

Alkynyl includes, for example, ethynyl, propargyl, 2-butynyl, 1-pentynyl and 2-pentynyl.

Preference is given to compounds of formula (1) wherein $R_5$ and $R_6$ are each independently of the other hydrogen or $C_1$–$C_{20}$alkyl, very especially hydrogen.

$R_1$ and $R_2$ in formula (1) are, each independently of the other, preferably hydrogen, unsubstituted or mono- or poly-halo-substituted $C_1$–$C_{20}$alkyl; or $C_1$–$C_5$alkoxy-$C_1$–$C_5$alkyl; especially hydrogen; unsubstituted or mono- or poly-halo-substituted $C_1$–$C_5$alkyl; or $C_1$–$C_3$alkoxy-$C_1$–$C_5$alkyl; and more especially hydrogen, methyl, ethyl, isopropyl, tert-butyl, $CF_3$ or the radical —$(CH_2)_m$—O—$CH_3$ wherein m is from 1 to 4.

$R_3$ in formula (1) is preferably unsubstituted or amino-substituted $C_7$–$C_{20}$alkyl, $C_3$–$C_7$cycloalkyl-$C_8$–$C_{20}$alkyl, $C_1$–$C_4$alkoxy-$C_7$–$C_{20}$alkyl, $R_7R_8N$—$C_7$–$C_{20}$alkyl, phenyl-$C_1$–$C_4$alkyl or phenyl-$C_1$–$C_6$alkoxy, especially unsubstituted or amino-substituted $C_7$–$C_{20}$alkyl or $R_7R_8N$—$C_7$–$C_{20}$alkyl.

Especially preferred compounds of formula (1) are those wherein $R_1$ and $R_2$ are each independently of the other hydrogen, methyl, ethyl, isopropyl, tert-butyl, $CF_3$ or the radical —$(CH_2)_m$—O—$CH_3$;

$R_3$ is unsubstituted or amino-substituted $C_7$–$C_{20}$alkyl or $R_7R_8N$—$C_7$–$C_{20}$alkyl;

$R_4$ is hydrogen or $C_1$–$C_{20}$alkyl;

$R_5$, $R_6$, $R_7$ and $R_8$ are each independently of the others hydrogen or $C_1$–$C_{20}$alkyl; and m is from 1 to 4, especially those wherein $R_5$, $R_6$, $R_7$ and $R_8$ are hydrogen.

Special preference is given to compounds of formulae

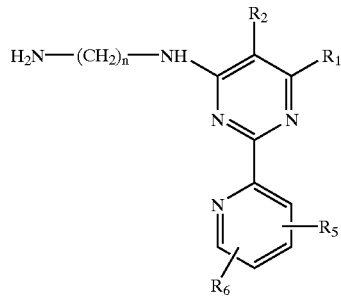

(2)

(3)

n is from 7 to 20; and $R_1$, $R_2$, $R_3$, $R_5$ and $R_6$ are as defined for formula (1).

All those compounds may also be present in the form of their acid addition salts, suitable acids being: HF, HCl, HBr, $H_2SO_4$, $H_3PO_4$, mono- and di-functional carboxylic acids, for example lactic acid, tartaric acid, acetic acid, maleic acid, fumaric acid, citric acid and salicylic acid, or sulfonic acid.

Table 1 below lists further 4-amino-2-(2-pyridyl)pyrimidines according to the invention by way of example:

TABLE 1

General formula

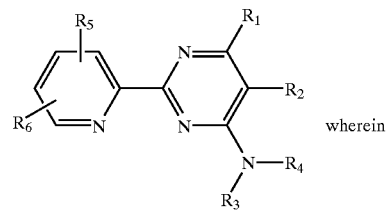

| Compound of formula | $R_1$ | $R_2$ | $R_3$ |
|---|---|---|---|
| 4 | —$CH_3$ | —$C_2H_5$ | —NH—$(CH_2)_7$—$NH_2$ |
| 5 | —$CH_3$ | —$C_2H_5$ | —NH—$(CH_2)_8$—$NH_2$ |
| 6 | —$CH_3$ | —$C_2H_5$ | —NH—$(CH_2)_9$—$NH_2$ |
| 7 | —$CH_3$ | —$C_2H_5$ | —NH—$(CH_2)_{12}$—$NH_2$ |
| 8 | —$CH_3$ | —$C_2H_5$ | —NH—$(CH_2)_6$—$CH_3$ |
| 9 | —$CH_3$ | —$C_2H_5$ | —NH—$(CH_2)_7$—$CH_3$ |
| 10 | —$CH_3$ | —$C_2H_5$ | —NH—$(CH_2)_8$—$CH_3$ |
| 11 | —$CH_3$ | —$C_2H_5$ | —NH—$(CH_2)_9$—$CH_3$ |
| 12 | —$CH_3$ | —$C_2H_5$ | —NH—$(CH_2)_{11}$—$CH_3$ |
| 13 | —$CH_3$ | —$C_2H_5$ | —NH—$(CH_2)_{15}$—$CH_3$ |
| 14 | —$CH_3$ | —$C_2H_5$ | (NH-cyclohexyl) |

TABLE 1-continued

General formula

| Compound of formula | $R_1$ | $R_2$ | $R_3$ |
|---|---|---|---|
| 15 | —$CH_3$ | —$C_2H_5$ | (NH-CH(CH_3)-CH_2-phenyl type, phenethylamino) |
| 16 | —$CH_3$ | —H | —NH—$(CH_2)_7$—$NH_2$ |
| 17 | —$CH_3$ | —H | —NH—$(CH_2)_8$—$NH_2$ |
| 18 | —$CH_3$ | —H | —NH—$(CH_2)_9$—$NH_2$ |
| 19 | —$CH_3$ | —H | —NH—$(CH_2)_{12}$—$NH_2$ |
| 20 | —$CH_3$ | —H | —NH—$(CH_2)_6$—$CH_3$ |
| 21 | —$CH_3$ | —H | —NH—$(CH_2)_7$—$CH_3$ |
| 22 | —$CH_3$ | —H | —NH—$(CH_2)_8$—$CH_3$ |
| 23 | —$CH_3$ | —H | —NH—$(CH_2)_9$—$CH_3$ |
| 24 | —$CH_3$ | —H | —NH—$(CH_2)_{11}$—$CH_3$ |
| 25 | —$CH_3$ | —H | —NH—$(CH_2)_{15}$—$CH_3$ |
| 26 | —$CH_3$ | —H | (NH-cyclohexyl) |
| 27 | —$CH_3$ | —H | (phenethylamino) |
| 28 | —$CF_3$ | —H | —NH—$(CH_2)_7$—$NH_2$ |
| 29 | —$CF_3$ | —H | —NH—$(CH_2)_8$—$NH_2$ |
| 30 | —$CF_3$ | —H | —NH—$(CH_2)_9$—$NH_2$ |
| 31 | —$CF_3$ | —H | —NH—$(CH_2)_{12}$—$NH_2$ |
| 32 | —$CF_3$ | —H | —NH—$(CH_2)_6$—$CH_3$ |
| 33 | —$CF_3$ | —H | —NH—$(CH_2)_7$—$CH_3$ |
| 34 | —$CF_3$ | —H | —NH—$(CH_2)_8$—$CH_3$ |
| 35 | —$CF_3$ | —H | —NH—$(CH_2)_9$—$CH_3$ |
| 36 | —$CF_3$ | —H | —NH—$(CH_2)_{11}$—$CH_3$ |
| 37 | —$CF_3$ | —H | —NH—$(CH_2)_{15}$—$CH_3$ |
| 38 | —$CF_3$ | —H | (NH-cyclohexyl) |
| 39 | —$CF_3$ | —H | (phenethylamino) |
| 40 | -isopropyl | —H | —NH—$(CH_2)_7$—$NH_2$ |
| 41 | -isopropyl | —H | —NH—$(CH_2)_8$—$NH_2$ |

TABLE 1-continued

General formula (Structure: pyrimidine with R$_3$ at 4-position, R$_2$ at 5-position, R$_1$ at 6-position, 2-position linked to 2-pyridyl)

| Compound of formula | R$_1$ | R$_2$ | R$_3$ |
|---|---|---|---|
| 42 | -isopropyl | —H | —NH—(CH$_2$)$_9$—NH$_2$ |
| 43 | -isopropyl | —H | —NH—(CH$_2$)$_{12}$—NH$_2$ |
| 44 | -isopropyl | —H | —NH—(CH$_2$)$_6$—CH$_3$ |
| 45 | -isopropyl | —H | —NH—(CH$_2$)$_7$—CH$_3$ |
| 46 | -isopropyl | —H | —NH—(CH$_2$)$_8$—CH$_3$ |
| 47 | -isopropyl | —H | —NH—(CH$_2$)$_9$—CH$_3$ |
| 48 | -isopropyl | —H | —NH—(CH$_2$)$_{11}$—CH$_3$ |
| 49 | -isopropyl | —H | —NH—(CH$_2$)$_{15}$—CH$_3$ |
| 50 | -isopropyl | —H | NH-cyclohexyl |
| 51 | -isopropyl | —H | HN-CH$_2$CH$_2$-phenyl |
| 52 | -tert-butyl | —H | —NH—(CH$_2$)$_7$—NH$_2$ |
| 53 | -tert-butyl | —H | —NH—(CH$_2$)$_8$—NH$_2$ |
| 54 | -tert-butyl | —H | —NH—(CH$_2$)$_9$—NH$_2$ |
| 55 | -tert-butyl | —H | —NH—(CH$_2$)$_{12}$—NH$_2$ |
| 56 | -tert-butyl | —H | —NH—(CH$_2$)$_6$—CH$_3$ |
| 57 | -tert-butyl | —H | —NH—(CH$_2$)$_7$—CH$_3$ |
| 58 | -tert-butyl | —H | —NH—(CH$_2$)$_8$—CH$_3$ |
| 59 | -tert-butyl | —H | —NH—(CH$_2$)$_9$—CH$_3$ |
| 60 | -tert-butyl | —H | —NH—(CH$_2$)$_{11}$—CH$_3$ |
| 61 | -tert-butyl | —H | —NH—(CH$_2$)$_{15}$—CH$_3$ |
| 62 | -tert-butyl | —H | NH-cyclohexyl |
| 63 | -tert-butyl | —H | HN-CH$_2$CH$_2$-phenyl |
| 64 | —CH$_3$ | -isopropyl | —NH—(CH$_2$)$_7$—NH$_2$ |
| 65 | —CH$_3$ | -isopropyl | —NH—(CH$_2$)$_8$—NH$_2$ |
| 66 | —CH$_3$ | -isopropyl | —NH—(CH$_2$)$_9$—NH$_2$ |
| 67 | —CH$_3$ | -isopropyl | —NH—(CH$_2$)$_{12}$—NH$_2$ |
| 68 | —CH$_3$ | -isopropyl | —NH—(CH$_2$)$_6$—CH$_3$ |
| 69 | —CH$_3$ | -isopropyl | —NH—(CH$_2$)$_7$—CH$_3$ |
| 70 | —CH$_3$ | -isopropyl | —NH—(CH$_2$)$_8$—CH$_3$ |
| 71 | —CH$_3$ | -isopropyl | —NH—(CH$_2$)$_9$—CH$_3$ |
| 72 | —CH$_3$ | -isopropyl | —NH—(CH$_2$)$_{11}$—CH$_3$ |
| 73 | —CH$_3$ | -isopropyl | —NH—(CH$_2$)$_{15}$—CH$_3$ |
| 74 | —CH$_3$ | -isopropyl | NH-cyclohexyl |
| 75 | —CH$_3$ | -isopropyl | HN-CH$_2$CH$_2$-phenyl |
| 76 | —(CH$_2$)$_2$—O—CH$_3$ | —H | —NH—(CH$_2$)$_7$—NH$_2$ |
| 77 | —(CH$_2$)$_2$—O—CH$_3$ | —H | —NH—(CH$_2$)$_8$—NH$_2$ |
| 78 | —(CH$_2$)$_2$—O—CH$_3$ | —H | —NH—(CH$_2$)$_9$—NH$_2$ |
| 79 | —(CH$_2$)$_2$—O—CH$_3$ | —H | —NH—(CH$_2$)$_{12}$—NH$_2$ |
| 80 | —(CH$_2$)$_2$—O—CH$_3$ | —H | —NH—(CH$_2$)$_6$—CH$_3$ |
| 81 | —(CH$_2$)$_2$—O—CH$_3$ | —H | —NH—(CH$_2$)$_7$—CH$_3$ |
| 82 | —(CH$_2$)$_2$—O—CH$_3$ | —H | —NH—(CH$_2$)$_8$—CH$_3$ |
| 83 | —(CH$_2$)$_2$—O—CH$_3$ | —H | —NH—(CH$_2$)$_9$—CH$_3$ |
| 84 | —(CH$_2$)$_2$—O—CH$_3$ | —H | —NH—(CH$_2$)$_{11}$—CH$_3$ |
| 85 | —(CH$_2$)$_2$—O—CH$_3$ | —H | —NH—(CH$_2$)$_{15}$—CH$_3$ |
| 86 | —(CH$_2$)$_2$—O—CH$_3$ | —H | NH-cyclohexyl |
| 87 | —(CH$_2$)$_2$—O—CH$_3$ | —H | HN-CH$_2$CH$_2$-phenyl |

TABLE 1-continued

General formula (R1, R2, R3 on pyrimidine ring connected to 2-pyridyl; R3 top, R2 middle, R1 bottom)

| Compound of formula | R₁ | R₂ | R₃ |
|---|---|---|---|
| 88 | —CH₃ | —C₂H₅ | —NH—CH₂—C₆H₅ (benzylamino) |
| 89 | —CH₃ | —C₂H₅ | —NH—(CH₂)₁₀—CH₃ |
| 90 | —CH₃ | —C₂H₅ | —NH—(CH₂)₁₄—CH₃ |
| 91 | —CH₃ | —H | —NH—CH₂—C₆H₅ (benzylamino) |
| 92 | —CH₃ | —H | —NH—(CH₂)₁₀—CH₃ |
| 93 | —CH₃ | —H | —NH—(CH₂)₁₄—CH₃ |
| 94 | —CF₃ | —H | —NH—CH₂—C₆H₅ (benzylamino) |
| 95 | —CF₃ | —H | —NH—(CH₂)₁₀—CH₃ |
| 96 | —CF₃ | —H | —NH—(CH₂)₁₄—CH₃ |
| 97 | -isopropyl | —H | —NH—CH₂—C₆H₅ (benzylamino) |
| 98 | -isopropyl | —H | —NH—(CH₂)₁₀—CH₃ |
| 99 | -isopropyl | —H | —NH—(CH₂)₁₄—CH₃ |

The novel 4-amino-2-(2-pyridyl)pyrimidines are prepared by methods known per se (J. Org. Chem.; 1967, 32, 1591). For that purpose, 2-cyanopyridine is reacted, in a suitable solvent, for example methanol, ethanol, isopropanol, DMF, tetrahydrofuran etc., with ammonium acetate or ammonium chloride at a temperature of from −10° C. to 100° C. over a period of from 1 hour to 24 hours to form the corresponding 2-amidinopyridine. The 2-amidinopyridine is then condensed with an appropriate β-keto ester using an auxiliary base, for example sodium carbonate, potassium hydroxide, sodium ethanolate, sodium methanolate, potassium tert-butanolate etc., in a suitable solvent, for example methanol, ethanol, butanol, tert-butanol, THF, DMF, acetonitrile, toluene, xylene etc., over a period of from 1 to 24 hours at a temperature of from 40 to 120° C. The 4-hydroxy-2-(2-pyridyl)pyrimidine thereby obtained is then converted into the corresponding 4-chloro-2-(2-pyridyl)pyrimidine by conventional methods using phosphorus oxychloride. The substituted 4-amino-2-(2-pyridyl)pyrimidines are obtained by reacting the 4-chloro-2-(2-pyridyl)pyrimidine with primary or secondary amines in a suitable solvent, for example DMF, dioxane, toluene, xylene, ethanol, butanol, and an auxiliary base, for example triethylamine, DIEA, sodium carbonate, potassium hydroxide etc., or using an excess of amine at from 40 to 130° C. over a period of from 1 to 24 hours. Preparation of the compounds of formula (2), except for the reaction with polymer-bound diamines, is analogous to that of compound (1). The polymer-bound diamines are obtained by reacting an excess of from 2 to 10 equivalents of diamine in, for example, DMF, dichloromethane, THF or dioxane with trityl chloride polystyrene resin at a temperature of from 10 to 50° C. over a period of from 0.5 to 24 hours. From 2 to 10 equivalents of appropriately substituted 4-chloro-2-(2-pyridyl)pyrimidines are then reacted, in a suitable solvent, for example dichloromethane, DMF, THF or toluene, with the polymer-bound diamines at from 10 to 120° C. over a period of from 2 to 48 hours. After washing the resin to remove the excess, the target compounds are split off using from 1 to 30% trifluoroacetic acid in dichloromethane at 25° C. over a period of from 1 to 5 hours. For the purpose of further purification, the substances are freeze-dried from tBuOH/water 4:1 with from 1 to 10% HOAc and once from tBuOH/water 4:1.

The entire reaction proceeds according to the following scheme, where the roman numerals in the reaction scheme refer to the reaction steps:

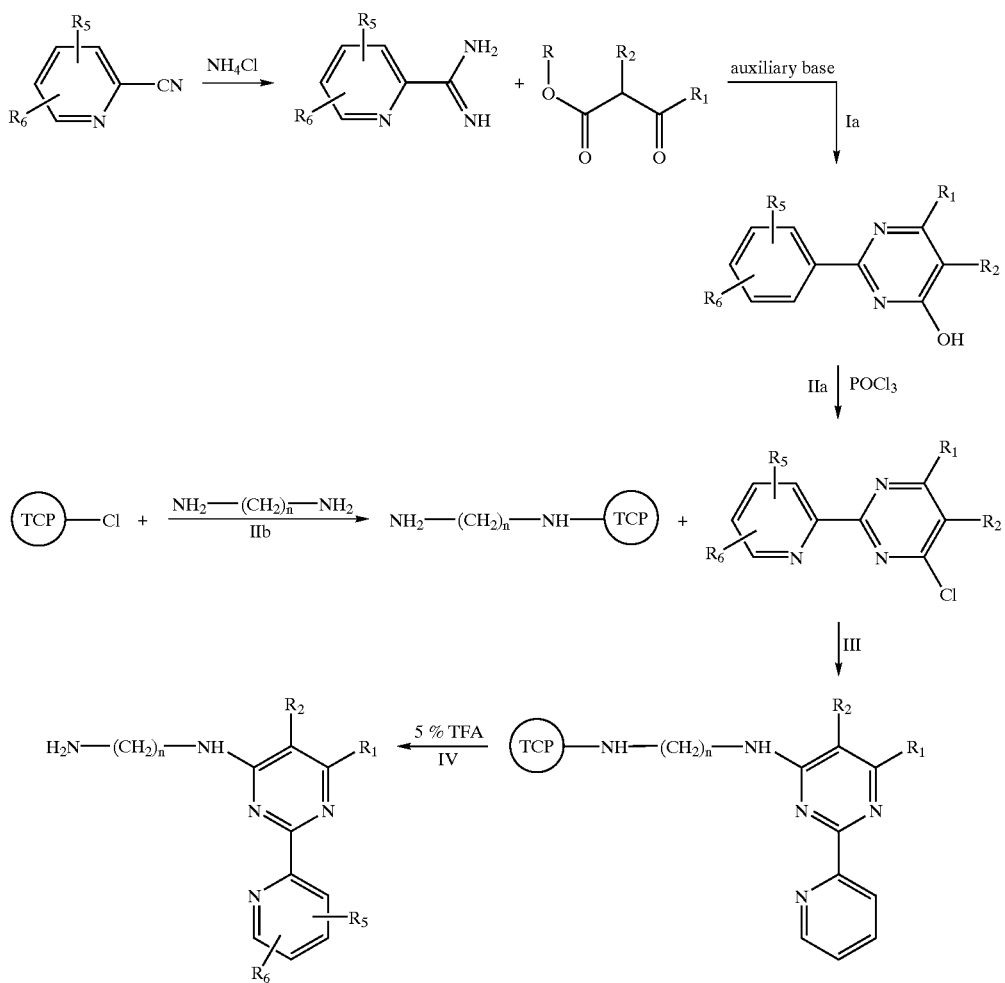

The compounds of formula (3) are prepared analogously to preparation of the compounds of formula (1) according to the following scheme, where the roman numerals in the reaction scheme refer to the reaction steps:

action, especially against pathogenic gram-positive and gram-negative bacteria and against bacteria of the skin flora, and also against yeasts and moulds. They are accordingly suitable especially for disinfection, deodorisation, and for

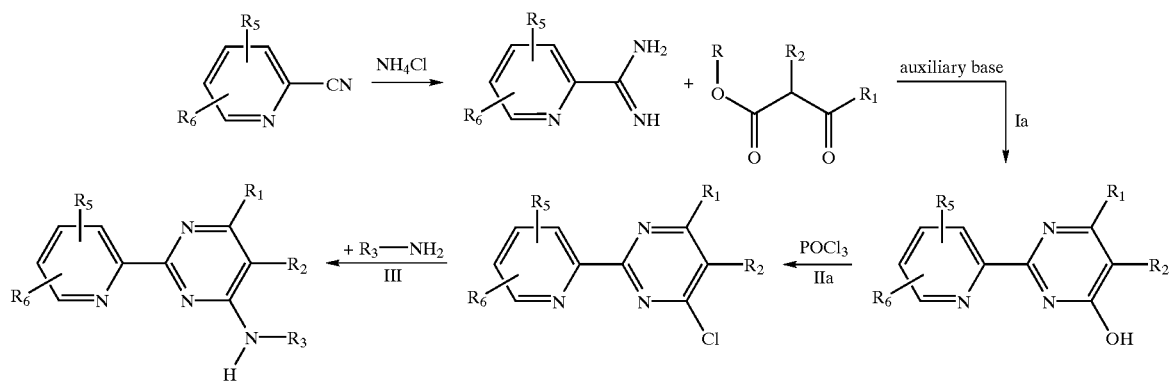

The 4-amino-2-(2-pyridyl)pyrimidines used in accordance with the invention exhibit pronounced antimicrobial general and antimicrobial treatment of the skin and mucosa and of integumentary appendages (hair), more especially for the disinfection of hands and wounds.

They are accordingly suitable as antimicrobial active substances and preservatives in personal care preparations, for example shampoos, bath additives, haircare preparations, liquid and solid soaps (based on synthetic surfactants and salts of saturated and/or unsaturated fatty acids), lotions and creams, deodorants, other aqueous or alcoholic solutions, e.g. cleansing solutions for the skin, moist cleaning cloths, oils or powders.

The invention accordingly relates also to a personal care preparation comprising at least one compound of formula (1) and cosmetically tolerable carriers or adjuvants.

The personal care preparation according to the invention contains from 0.01 to 15% by weight, preferably from 0.1 to 10% by weight, based on the total weight of the composition, of a compound of formula (1), and cosmetically tolerable adjuvants.

Depending upon the form of the personal care preparation, it comprises, in addition to the 4-amino-2-(2-pyridyl) pyrimidine of formula (1), further constituents, for example sequestering agents, colourings, perfume oils, thickening or solidifying agents (consistency regulators), emollients, UV-absorbers, skin protective agents, antioxidants, additives that improve the mechanical properties, such as dicarboxylic acids and/or aluminium, zinc, calcium or magnesium salts of $C_{14}$–$C_{22}$ fatty acids, and, optionally, preservatives.

The personal care preparation according to the invention may be in the form of a water-in-oil or oil-in-water emulsion, an alcoholic or alcohol-containing formulation, a vesicular dispersion of an ionic or non-ionic amphiphilic lipid, a gel, a solid stick or an aerosol formulation.

As a water-in-oil or oil-in-water emulsion, the cosmetically tolerable adjuvant contains preferably from 5 to 50% of an oil phase, from 5 to 20% of an emulsifier and from 30 to 90% water. The oil phase may comprise any oil suitable for cosmetic formulations, for example one or more hydrocarbon oils, a wax, a natural oil, a silicone oil, a fatty acid ester or a fatty alcohol. Preferred mono- or poly-ols are ethanol, isopropanol, propylene glycol, hexylene glycol, glycerol and sorbitol.

Cosmetic formulations according to the invention are used in various fields. There come into consideration, for example, especially the following preparations:

skin-care preparations, e.g. skin-washing and cleansing preparations in the form of tablet-form or liquid soaps, synthetic detergents or washing pastes, bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eyeshadow preparations, mascaras, eyeliners, eye creams or eye-fix creams; lip-care preparations, e.g. lipsticks, lip gloss, lip contour pencils, nail-care preparations, such as nail varnish, nail varnish removers, nail hardeners or cuticle removers;

intimate hygiene preparations, e.g. intimate washing lotions or intimate sprays;

foot-care preparations, e.g. foot baths, foot powders, foot creams or foot balsams, special deodorants and antiperspirants or callus-removing preparations;

light-protective preparations, such as sun milks, lotions, creams or oils, sun-blocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, perfume), perfume oils or perfume creams;

dental care, denture-care and mouth-care preparations, e.g. toothpastes, gel toothpastes, tooth powders, mouthwash concentrates, anti-plaque mouthwashes, denture cleaners or denture fixatives;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidising dyes, or natural hair colorants, such as henna or camomile.

An antimicrobial soap has, for example, the following composition:

0.01 to 5% by weight of a compound of formula (1)

0.3 to 1% by weight titanium dioxide, 1 to 10% by weight stearic acid, soap base ad 100%, e.g. a sodium salt of tallow fatty acid or coconut fatty acid, or glycerol.

A shampoo has, for example, the following composition:

0.01 to 5% by weight of a compound of formula (1), 12.0% by weight sodium laureth-2-sulfate, 4.0% by weight cocamidopropyl betaine, 3.0% by weight NaCl and water ad 100%.

A deodorant has, for example, the following composition:

0.01 to 5% by weight of a compound of formula (1),

60% by weight ethanol, 0.3% by weight perfume oil, and water ad 100%.

The invention relates also to an oral composition containing from 0.01 to 15% by weight, based on the total weight of the composition, of a compound of formula (1), and orally tolerable adjuvants.

Example of an Oral Composition:

10% by weight sorbitol,
10% by weight glycerol,
15% by weight ethanol,
15% by weight propylene glycol,
0.5% by weight sodium lauryl sulfate,
0.25% by weight sodium methylcocyl taurate,
0.25% by weight polyoxypropylene/polyoxyethylene block copolymer,
0.10% by weight peppermint flavouring,
0.1 to 0.5% by weight of a compound of formula (1), and
48.6% by weight water.

The oral composition according to the invention may be, for example, in the form of a gel, a paste, a cream or an aqueous preparation (mouthwash).

The oral composition according to the invention may also comprise compounds that release fluoride ions which are effective against the formation of caries, for example inorganic fluoride salts, e.g. sodium, potassium, ammonium or calcium fluoride, or organic fluoride salts, e.g. amine fluorides, which are known under the trade name Olafluor.

The 4-amino-2-(2-pyridyl)pyrimidines of formula (1) used in accordance with the invention are also suitable for treating, especially preserving, textile fibre materials. Such materials are undyed and dyed or printed fibre materials, e.g. of silk, wool, polyamide or polyurethanes, and especially cellulosic fibre materials of all kinds. Such fibre materials are, for example, natural cellulose fibres, such as cotton, linen, jute and hemp, as well as cellulose and regenerated cellulose. Preferred suitable textile fibre materials are made of cotton.

The 4-amino-2-(2-pyridyl)pyrimidines according to the invention are suitable also for treating, especially imparting antimicrobial properties to or preserving, plastics, e.g. polyethylene, polypropylene, polyurethane, polyester, polyamide, polycarbonate, latex etc. Fields of use therefor are, for example, floor coverings, plastics coatings, plastics containers and packaging materials; kitchen and bathroom utensils (e.g. brushes, shower curtains, sponges, bathmats), latex, filter materials (air and water filters), plastics articles used in the field of medicine, e.g. dressing materials, syringes, catheters etc., so-called "medical devices", gloves and mattresses.

Paper, for example papers used for hygiene purposes, may also be provided with antimicrobial properties using the 4-amino-2-(2-pyridyl)pyrimidines according to the invention.

It is also possible for nonwovens, e.g. nappies/diapers, sanitary towels, panty liners, and cloths for hygiene and household uses, to be provided with antimicrobial properties in accordance with the invention.

The 4-amino-2-(2-pyridyl)pyrimidines of formula (1) are also used in washing and cleaning formulations, e.g. in liquid or powder washing agents or softeners.

The 4-amino-2-(2-pyridyl)pyrimidines of formula (1) can also be used especially in household and general-purpose cleaners for cleaning and disinfecting hard surfaces.

A cleaning preparation has, for example the following composition:

0.01 to 5% by weight of a compound of formula (1)
3.0% by weight octyl alcohol 4EO
1.3% by weight fatty alcohol $C_8$–$C_{10}$polyglucoside
3.0% by weight isopropanol
water ad 100%.

In addition to preserving cosmetic and household products, the preservation of technical products, the provision of technical products with antimicrobial properties and use as a biocide in technical processes are also possible, for example in paper treatment, especially in paper treatment liquors, printing thickeners of starch or cellulose derivatives, surface-coatings and paints.

The 4-amino-2-(2-pyridyl)pyrimidines of formula (1) are also suitable for the antimicrobial treatment of wood and for the antimicrobial treatment of leather, the preserving of leather and the provision of leather with antimicrobial properties.

The compounds according to the invention are also suitable for the protection of cosmetic products and household products from microbial damage.

The following Examples illustrate, but do not limit, the present invention.

PREPARATION EXAMPLES

Example 1

Synthesis of Substituted
4-amino-2-(2-pyridyl)pyrimidines

1a: Preparation of 2-(2-pyridyl)pyrimidines

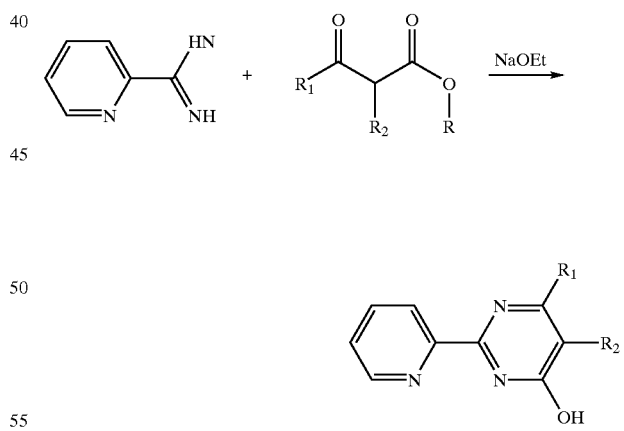

Sodium (1.44 g; 63 mmol) is dissolved, under nitrogen, in absolute ethanol (28.8 ml) at 45° C. A solution of 2-amidinopyridine hydrochloride (9.8 g; 63 mmol) in abs. ethanol (35 ml) is added and the mixture is heated at reflux for 1 hour. Portions, each of 8 ml, of the suspension are transferred to 8 flasks each containing a β-keto ester (7.88 mmol) in abs. ethanol (5 ml) (see Table 2 for amounts used). The suspensions are heated at reflux for 5 hours. After cooling to 25° C., the reaction mixture is evaporated to dryness and directly used in chlorination.

TABLE 2

β-Keto esters used

| β-Keto ester | R₁ | R₂ | R | Amount used |
|---|---|---|---|---|
| 2-ethylacetoacetic acid ethyl ester | —CH₃ | —C₂H₅ | —C₂H₅ | 1.27 g |
| acetoacetic acid ethyl ester | —CH₃ | H | —C₂H₅ | 1.04 g |
| trifluoroacetoacetic acid methyl ester | —CF₃ | H | —CH₃ | 1.36 g |
| 4-methyl-3-oxopentanoic acid methyl ester | -isopropyl | —CF₃ | —CH₃ | 1.27 g |
| 4,4-dimethyl-3-oxopentanoic acid methyl ester | -tert-butyl | H | —CH₃ | 1.27 g |
| 2-isopropylacetoacetic acid ethyl ester | —CH₃ | —isopropyl | —C₂H₅ | 1.38 g |
| 5-methoxy-3-oxopentanoic acid methyl ester | H₃C—O—CH₂—CH₂— | H | —CH₃ | 1.28 g |
| benzoylacetic acid ethyl ester | phenyl | H | —C₂H₅ | 1.54 g | b: Synthesis of 4-chloro-2-(2-pyridyl)pyrimidines

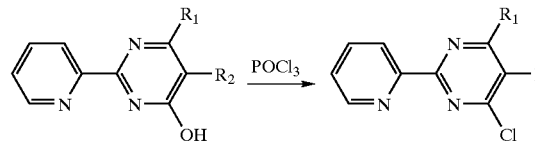

The crude products from a) are taken up in phosphorus oxychloride (5 ml, 54 mmol, in each case) and heated at 110° C. for 3 hours. After cooling to 25° C., the reaction mixtures are poured into 10 ml of ice-water and slowly adjusted to pH 8–9 using aqueous sodium hydroxide solution. The crude products obtained are extracted with dichloromethane (5×10 ml) and the organic extracts are washed with water (2×10 ml) and with saturated NaCl solution. After drying over MgSO₄, the product is filtered off and evaporated to dryness. Because of the good purity of most of the products (see Table 3), further processing is carried out without further purification.

TABLE 3

HPLC purity of crude products (detection at 214 nm)

| No. | R₁ | R₂ | HPLC purity [%] |
|---|---|---|---|
| 1 | —CH₃ | —Et | >99 |
| 2 | —CH₃ | —H | >99 |
| 3 | —CF₃ | —H | >99 |
| 4 | -isopropyl | —H | >99 |
| 5 | -tert-butyl | —H | 93 |
| 6 | —CH₃ | -iPr | 83 |
| 7 | —CH₂CH₂—O—CH₃ | —H | 98 |
| 8 | -phenyl | —H | <5 | c: Loading of Trityl Chloride-Polystyrene Resin (TCP) with Diamines

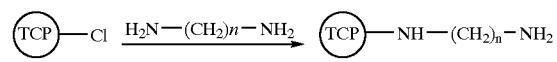

In each case, 1 g of TCP resin (resin loading: 1.44 mmol/g) was shaken in abs. dichloromethane (5 ml) with a diamine (see Tab. 4; 5 equiv.; 7.2 mmol) for 24 hours at 25° C. The resin is washed with dichloromethane (5×), 1% HOAc/DCM, DMF and diethyl ether and dried in vacuo.

TABLE 4

Diamines used and weights thereof

| diamine | amount used |
|---|---|
| n = 7 | 938 mg |
| n = 8 | 1039 mg |
| n = 9 | 1140 mg |
| n = 12 | 1443 mg | d: Reaction of the Diamine-TCP Resins with 4-chloro-2-(2-pyridyl)pyrimidines

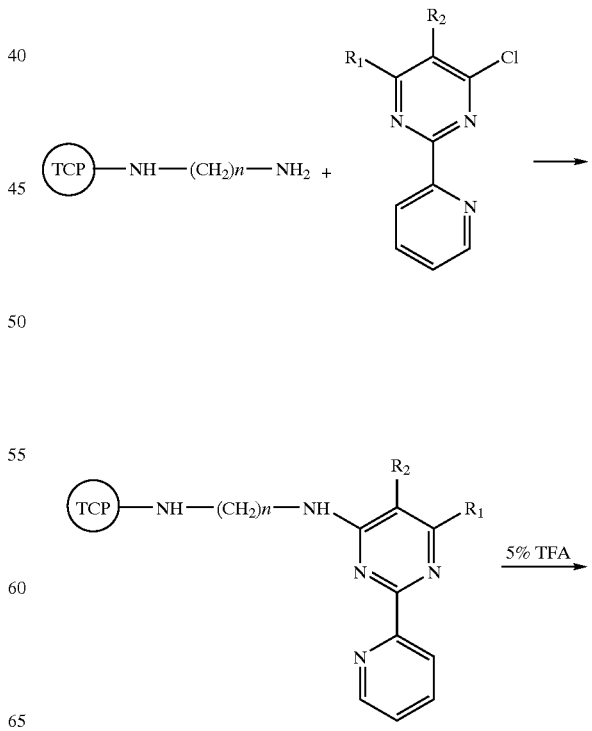

-continued

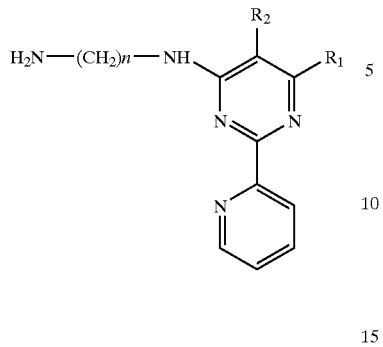

Diamine-TCP resins (50 mg; 72 μmol of diamine, in each case) are shaken in abs. dichloromethane (1 ml, in each case) with 4-chloro-2-(2-pyridyl)pyrimidines (3 equiv.; 216 μmol, in each case) and DIPEA (5 equiv.; 360 μmol) for 48 hours at 25° C. The resin is then filtered off, washed (DMF 5×, MeOH 5×, DCM 5×, diethyl ether 5×) and dried in vacuo. Cleaving is then carried out using 5% TFA/DCM (1.5 mL, in each case) for 1 hour at 25° C. The cleavage solutions are evaporated to dryness and the crude products are freeze-dried from tBuOH/water 4:1 with 10% HOAc and once from tBuOH/water 4:1.

e: Reaction of 4-chloro-2-(2-pyridyl)pyrimidines with monoamines

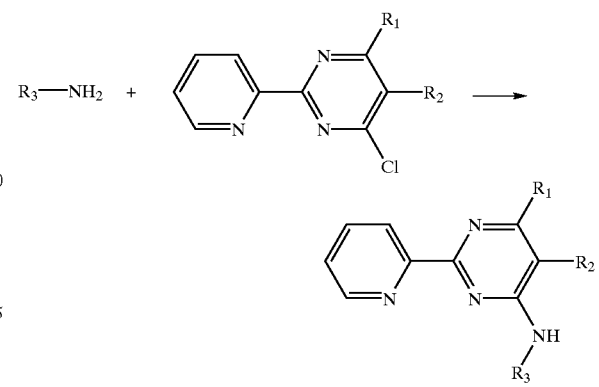

4-Chloro-2-(2pyridyl)pyrimidines (72 μmol, in each case) are heated with monoamines (3 equiv.; 216 μmol, in each case) in abs. dioxane (0.5 ml) for 24 hours at 90° C. After cooling to 25° C., in order to remove the excess of amine, a scavenger resin (polystyrene aldehyde resin; resin loading 1.28 mmol/g; 3 equiv; 216 mmol; 170 mg) and also trimethyl orthoformate (2 equiv.; 144 μmol; 15 mg; 16 μl) and additional abs. THF (2 ml) are added. The reaction mixture is shaken for 24 hours at 25° C. After filtering, the filtrate is evaporated to dryness and the crude product is freeze-dried from tBuOH/water 4:1 with 10% HOAc and once from tBuOH/water 4:1.

TABLE 5

Amines and amounts used

| Amine | Amount (216 μmol) | Amine | Amount (216 μmol) |
|---|---|---|---|
| $H_2N\text{-}(CH_2)_6\text{-}CH_3$ | 25 mg; 32 μL | $H_2N\text{-}(CH_2)_{10}\text{-}CH_3$ | 37 mg; 46 μL |
| $H_2N\text{-}(CH_2)_7\text{-}CH_3$ | 28 mg; 36 μL | $H_2N\text{-}(CH_2)_{14}\text{-}CH_3$ | 49 mg |
| $H_2N\text{-}(CH_2)_8\text{-}CH_3$ | 31 mg; 40 μL | benzylamine | 23 mg; 24 μL |
| $H_2N\text{-}(CH_2)_9\text{-}CH_3$ | 34 mg; 43 μL | cyclohexylamine | 21 mg; 25 μL |
| $H_2N\text{-}(CH_2)_{11}\text{-}CH_3$ | 40 mg; 50 μL | phenylethylamine | 26 mg; 29 μL |
| $H_2N\text{-}(CH_2)_{15}\text{-}CH_3$ | 52 mg | | |

All compounds prepared by the methods described above are listed in Tab. 1 and were characterised by means of HPLC and MS (Table 7, Purities). Some of the compounds were analysed using $^1$H-NMR spectroscopy (Table 6):

TABLE 6

| Comp. of f. | Structure | $^1$H-NMR 250 MHz (CD$_3$OD), δ [ppm]: | | |
|---|---|---|---|---|
| | | δ [ppm] | Multiplicity | Assignment |
| (35) | 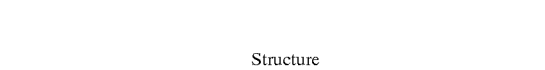 | 0.80–1.75 | m, 19 H | —NH—CH—CH$_2$— |
| | | 3.64 | t, 2 H (J = 7 Hz) | H arom. |
| | | 6.87 | s, 1 H | H arom. |
| | | 7.78 | m, 1 H | H arom. |
| | | 8.26 | m, 1 H | H arom. |
| | | 8.63 | m, 1 H | H arom. |
| | | 8.76 | m, 1 H | H arom. |

TABLE 6-continued

| Comp. of f. | Structure | δ [ppm] | Multiplicity | Assignment |
|---|---|---|---|---|
| | | \(^1\)H-NMR 250 MHz (CD\(_3\)OD), δ [ppm]: | | |
| (36) | F₃C-pyrimidine-NH-(CH₂)₁₁-CH₃ with 2-pyridyl | 0.80–1.75<br>3.63<br>6.87<br>7.73<br>8.21<br>8.62<br>8.77 | m, 23 H<br>t, 2 H (J = 7 Hz)<br>s, 1 H<br>m, 1 H<br>m, 1 H<br>m, 1 H<br>m, 1 H | —NH—CH—CH₂—<br>H arom.<br>H arom.<br>H arom.<br>H arom.<br>H arom.<br>H arom. |
| (37) | F₃C-pyrimidine-NH-(long chain) with 2-pyridyl | 0.80–1.73<br>3.63<br>6.85<br>7.68<br>8.15<br>8.59<br>8.73 | m, 31 H<br>t, 2 H (J = 7 Hz)<br>s, 1 H<br>m, 1 H<br>m, 1 H<br>m, 1 H<br>m, 1 H | —NH—CH—CH₂—<br>H arom.<br>H arom.<br>H arom.<br>H arom.<br>H arom.<br>H arom. |
| (44) | iPr-pyrimidine-NH-(CH₂)₆-CH₃ with 2-pyridyl | 0.80–1.80<br>3.72<br>6.61<br>7.73<br>8.13<br>8.58<br>8.87 | m, 20 H<br>t, 2 H (J = 7 Hz)<br>s, 1 H<br>m, 1 H<br>m, 1 H<br>m, 1 H<br>m, 1 H | —NH—CH—CH₂—<br>H arom.<br>H arom.<br>H arom.<br>H arom.<br>H arom.<br>H arom. |
| (47) | iPr-pyrimidine-NH-(long chain) with 2-pyridyl | 0.70–1.70<br>3.56<br>6.44<br>7.57<br>7.96<br>8.40<br>8.69 | m, 26 H<br>t, 2 H (J = 7 Hz)<br>s, 1 H<br>m, 1 H<br>m, 1 H<br>m, 1 H<br>m, 1 H | —NH—CH—CH₂—<br>H arom.<br>H arom.<br>H arom.<br>H arom.<br>H arom.<br>H arom. |

Example 2

Determination of the Minimum Inhibitory Concentration (MIC Value) in Microtitre Plates Nutrient Medium:

Casein-soybean flour-peptone broth for preparation of pre-cultures of test bacteria and yeast.

Mycological slant agar for the pre-culture of moulds

Examples of Test Organisms:

| Bacteria: | *Staphylococcus hominis* DMS 20328 (= SH)<br>*Escherichia coli* NCTC 8196 (= EC) |
|---|---|

Procedure:

The test substances are pre-dissolved in dimethyl sulfoxide (DMSO) and tested in a dilution series of 1:2.

Bacteria and yeast are cultured overnight in CASO broth, the mould is cultured overnight on mycological slant agar, and washed off using 10 ml of 0.85% sodium chloride solution (+0.1% Triton X-100).

All the test organisms are adjusted to an organism count of 1–5×10⁶ CFU/ml using 0.85% sodium chloride solution.

The test substances are pre-pipetted into microtitre plates in amounts of 8 μl per well.

Pre-diluted organism suspensions are diluted 1:100 in CASO broth (bacteria and yeast) or Sabouraud 2% glucose broth (mould) and are added in amounts of 192 μl per well to the test substances.

The test batches are incubated for 48 hours at 37° C. (bacteria and yeast) or for 5 days at 28° C. (mould).

After incubation, the growth is determined on the basis of the turbidity of the test batches (optical density) at 620 nm in a microplate reader.

The minimum inhibitory concentration (MIC value) is the concentration of substance at which there is found (compared to the growth of the control) an appreciable inhibition of growth (≦20% growth) of the test organisms.

One microtitre plate is used for each test organism and substance concentration. All the substances are tested in duplicate.

The results are compiled in Table 7:

TABLE 7

Minimum inhibitory concentration (MIC) of compounds tested [μg]

| Comp. of formula | Purity [%] | S. hominis [μg/mL] | E. coli [μg/mL] | No. | Purity [%] | S. hominis [μg/mL] | E. coli [μg/mL] |
|---|---|---|---|---|---|---|---|
| 4 | 69 | >120 | >120 | 53 | 92 | 80 | >80 |
| 5 | 63 | >120 | >120 | 54 | 99 | 30 | 120 |
| 6 | 63 | n. d. | n. d. | 55 | 66 | 7.5 | 60 |
| 7 | 60 | 120 | 120 | 56 | 89 | 3.75 | >120 |
| 8 | 98 | n. d. | n. d. | 57 | 88 | 3.75 | >120 |
| 9 | 74 | 7.5 | >120 | 58 | 88 | 3.75 | >120 |
| 10 | 79 | 5 | >80 | 59 | 96 | n. d. | n. d. |
| 11 | 78 | 3.75 | >120 | 60 | 94 | 3.75 | 120 |
| 12 | 98 | 7.5 | 120 | 61 | 71 | >120 | >120 |
| 13 | 95 | 120 | >120 | 62 | 90 | n. d. | n. d. |
| 14 | 95 | 120 | >120 | 63 | 90 | 3.75 | >120 |
| 15 | 65 | 60 | >120 | 64 | 80 | 30 | >120 |
| 16 | 95 | >120 | >120 | 65 | 91 | 30 | 120 |
| 17 | 91 | >80 | >80 | 66 | 87 | 3.75 | 30 |
| 18 | 94 | 120 | >120 | 67 | 82 | 5 | 20 |
| 19 | 93 | 15 | 60 | 68 | 83 | 7.5 | >120 |
| 20 | 95 | 7.5 | 120 | 69 | 93 | 3.75 | 120 |
| 21 | 95 | 3.75 | 60 | 70 | 74 | 3.75 | >120 |
| 22 | 95 | 3.75 | 120 | 71 | 71 | 5 | >80 |
| 23 | 95 | 3.75 | >120 | 72 | 77 | 15 | >120 |
| 24 | 93 | 2.5 | 80 | 73 | 67 | 120 | >120 |
| 25 | 90 | 15 | >120 | 74 | 85 | 60 | >120 |
| 26 | 95 | 60 | >120 | 75 | 53 | 30 | >120 |
| 27 | 96 | 60 | >120 | 76 | 95 | 40 | >80 |
| 28 | 98 | >80 | >80 | 77 | 92 | 30 | 120 |
| 29 | >99 | >80 | >80 | 78 | 64 | 15 | 60 |
| 30 | 99 | 120 | 120 | 79 | 69 | 10 | 20 |
| 31 | 98 | 5 | 20 | 80 | 71 | 30 | >120 |
| 32 | 99 | 3.75 | >120 | 81 | 87 | 15 | >120 |
| 33 | 99 | 2.5 | >80 | 82 | 70 | 7.5 | 120 |
| 34 | 99 | 3.75 | >120 | 83 | 65 | 7.5 | >120 |
| 35 | 99 | 3.75 | >120 | 84 | 56 | 15 | 120 |
| 36 | 98 | 60 | >120 | 85 | 73 | 120 | 120 |
| 37 | 90 | >120 | >120 | 86 | 75 | 120 | >120 |
| 38 | 99 | 60 | >120 | 87 | 62 | 30 | 120 |
| 39 | 99 | 30 | >120 | 88 | 90 | 120 | 120 |
| 40 | 75 | 120 | >120 | 89 | 91 | 3.75 | >120 |
| 41 | 94 | 120 | >120 | 90 | 87 | 30 | 120 |
| 42 | 99 | 30 | 120 | 91 | 80 | 30 | >120 |
| 43 | 91 | 7.5 | 60 | 92 | 84 | 3.75 | >120 |
| 44 | 97 | 3.75 | >120 | 93 | 83 | 7.5 | >120 |
| 45 | 97 | 3.75 | >120 | 94 | 83 | >120 | >120 |
| 46 | 97 | 3.75 | >120 | 95 | 79 | 120 | >120 |
| 47 | 97 | 5 | >80 | 96 | 88 | 120 | 120 |
| 48 | 80 | 3.75 | 120 | 97 | 90 | 15 | 120 |
| 49 | 90 | >120 | >120 | 98 | 81 | 3.75 | >120 |
| 50 | 94 | 15 | >120 | 99 | 80 | 15 | >120 |
| 51 | 95 | 30 | >120 | | | | |
| 52 | 80 | n. d. | n. d. | | | | | n. d. = not determined
Purity [%] = HPLC area percentages at a detection wavelength of 214 nm

TABLE 8

Minimum inhibitory concentrations (MIC in [μg/mL]) of selected compounds with respect to further microorganisms

| Microorganism | \multicolumn{11}{c}{Compound of formula} |
|---|---|---|---|---|---|---|---|---|---|---|---|
| | 37 | 44 | 68 | 45 | 46 | 70 | 23 | 47 | 63 | 71 | 32 |
| Staphylococcus aureus ATCC 9144 | 15* | 15 | 15 | 7.5 | 30 | 7.5 | 7.5 | 7.5 | 15 | 7.5 | 15 |
| S. epidermidis ATCC 12228 | 7.5 | 15 | 15 | 7.5 | 30 | 7.5 | 7.5 | 3.75 | 30 | 7.5 | 7.5 |
| Micrococcus luteus ATCC 9341 | 1.0 | 1.0 | 3.75 | 3.75 | 3.75 | 1.0 | <0.5 | <0.5 | 7.5 | 1.9 | >0.5 |
| Enterococcus hirae ATCC 10541 | 30 | 15 | 7.5 | 3.75 | 30 | 3.75 | 3.75 | 3.75 | 30 | 7.5 | 7.5 |
| E. coli NCTC 8196 | >30 | >30 | >30 | >30 | >60 | >60 | >60 | >60 | *60 | >60 | >60 |
| Epidermophyton floccosum DSM 10709 | >60 | 60 | 60* | >60 | 60 | *7.5 | *15 | *60 | *15 | 60 | *60 |
| Trichophyton mentagrophytes ATCC 9533 | >60 | >60 | >60 | >60 | >60 | 15 | 15 | 60 | *60 | *30 | >60 |

| Microorganism | \multicolumn{10}{c}{Compound of formula} |
|---|---|---|---|---|---|---|---|---|---|---|
| | 56 | 9 | 33 | 57 | 10 | 34 | 58 | 11 | 35 | 43 | 83 |
| Staphylococcus aureus ATCC 9144 | 3.75 | 15 | 15 | 1.9 | 15 | >60 | *1.9 | 7.5 | *7.5 | 30 | *15 |
| S. epidermidis ATCC 12228 | 3.75 | *15 | 3.75 | 1.9 | 15 | *60 | 1.9 | 7.5 | 7.5 | *15 | 15 |
| Micrococcus luteus ATCC 9341 | <0.5 | 3.75 | <0.5 | <0.5 | <0.5 | >0.5 | <0.5 | 1.9 | <0.5 | 3.75 | 3.75 |
| Enterococcus hirae ATCC 10541 | 1.9 | 30 | 15 | 1.0 | 30 | 60 | 7.5 | 7.5 | 7.5 | 30 | 30 |
| E. coli NCTC 8196 | >60 | >60 | >60 | >60 | >60 | >60 | >60 | >60 | >60 | >60 | >60 |
| Epidermophyton floccosum DSM 10709 | *30 | *15 | >60 | 60 | 60 | >60 | >60 | >60 | >60 | >60 | >60 |
| Trichophyton mentagrophytes ATCC 9533 | *30 | *30 | >60 | *60 | 60 | >60 | >60 | >60 | >60 | >60 | >60 |

| Microorganism | \multicolumn{10}{c}{Compound of formula} |
|---|---|---|---|---|---|---|---|---|---|---|
| | 12 | 60 | 21 | 69 | 77 | 22 | 30 | 54 | 78 | 7 | |
| Staphylococcus aureus ATCC 9144 | 15 | 15 | 120 | 7.5 | >60 | 7.5 | >60 | *60 | *60 | >60 | |
| S. epidermidis ATCC 12228 | *7.5 | *7.5 | 120 | 7.5 | >60 | <3.75 | >60 | >60 | *60 | >60 | |
| Micrococcus luteus ATCC 9341 | <3.75 | <3.75 | 120 | <3.75 | >60 | <3.75 | 60 | 15 | >60 | >60 | |
| Enterococcus hirae ATCC 10541 | 7.5 | 7.5 | 120 | 3.75 | >60 | <3.75 | >60 | >60 | >60 | >60 | |
| E. coli NCTC 8196 | >60 | >60 | 120 | >60 | >60 | >60 | >60 | >60 | >60 | >60 | |
| Klebsiella pneumonia ATCC 4352 | >60 | >60 | 120 | *60 | >60 | >60 | >60 | >60 | >60 | >60 | |
| Salmonella choleraesuis ATCC 10708 | >60 | >60 | >120 | >60 | >60 | >60 | >60 | >60 | >60 | >60 | |
| Pseudomonas aeruginosa CIP A-22 | >60 | >60 | >120 | >60 | >60 | >60 | >60 | >60 | >60 | >60 | |
| Candida albicans ATCC 10231 | *60 | >60 | 120 | 60 | >60 | 15 | >60 | >60 | >60 | >60 | |
| Aspergillus niger ATCC 6275 | >60 | 60 | >60 | *60 | >60 | 60 | >60 | >60 | >60 | >30 | |
| Epidermophyton floccosum DSM 10709 | *30 | >60 | >60 | 15 | >60 | *7.5 | >60 | >60 | >60 | >30 | |
| Trichophyton mentagrophytes ATCC 9533 | 60 | >60 | >60 | *15 | >60 | 15 | >60 | >60 | >60 | >30 | |

| Microorganism | \multicolumn{8}{c}{Compound of formula} |
|---|---|---|---|---|---|---|---|---|
| | 79 | 24 | 48 | 65 | 18 | 42 | 66 | 19 |
| Staphylococcus aureus ATCC 9144 | *60 | <3.75 | <3.75 | >60 | >60 | 60 | 60 | 60 |
| S. epidermidis ATCC 12228 | 30 | 3.75 | <3.75 | >60 | >60 | 60 | 60 | 60 |
| Micrococcus luteus ATCC 9341 | 60 | <3.75 | <3.75 | >60 | >60 | *15 | *30 | 7.5 |
| Enterococcus hirae ATCC 10541 | >60 | *15 | <3.75 | >60 | >60 | >60 | >60 | 60 |
| E. coli NCTC 8196 | 60 | >60 | >60 | >60 | >60 | >60 | >60 | >60 |
| Klebsiella pneumonia ATCC 4352 | >60 | >60 | >60 | >60 | >60 | >60 | >60 | >60 |
| Salmonella choleraesuis ATCC 10708 | >60 | >60 | >60 | >60 | >60 | >60 | >60 | >60 |
| Pseudomonas aeruginosa CIP A-22 | >60 | >60 | >60 | >60 | >60 | >60 | >60 | >60 |

| Microorganism | \multicolumn{8}{c}{Compound of formula} |
|---|---|---|---|---|---|---|---|---|
| | 79 | 24 | 48 | 65 | 18 | 42 | 66 | 19 |
| Candida albicans ATCC 10231 | *30 | 30 | *15 | >60 | >60 | >60 | >60 | 7.5 |
| Aspergillus niger ATCC 6275 | >60 | >60 | >60 | >60 | >60 | >60 | >60 | >60 |
| Epidermophyton floccosum DSM 10709 | >60 | 60 | *60 | >60 | >60 | >60 | >60 | >60 |
| Trichophyton mentagrophytes ATCC 9533 | >60 | >60 | *60 | >60 | >60 | >60 | >60 | >60 |

| Microorganism | \multicolumn{6}{c}{Compound of formula} |
|---|---|---|---|---|---|---|
| | 92 | 93 | 89 | 90 | 98 | 99 |
| Staphylococcus aureus ATCC 9144 | 3.75 | 15 | 7.5 | *30 | 1.9 | 7.5 |
| S. epidermidis ATCC 12228 | *1.9 | 7.5 | 7.5 | *30 | 1.9 | 3.75 |
| Micrococcus luteus ATCC 9341 | <0.5 | 1.9 | 1.9 | 15 | <0.5 | 1.0 |
| Enterococcus hirae ATCC 10541 | 3.75 | 15 | 7.5 | 30 | 1.9 | 3.75 |
| E. coli NCTC 8196 | >120 | >120 | >60 | >60 | 120 | >60 |
| Klebsiella pneumonia ATCC 4352 | 120 | >120 | 60 | >60 | 120 | >60 |
| Salmonella choleraesuis ATCC 10708 | >120 | >120 | >60 | >60 | >120 | >60 |
| Pseudomonas aeruginosa CIP A-22 | >120 | >120 | >60 | >60 | >120 | >60 |

TABLE 8-continued

Minimum inhibitory concentrations (MIC in [µg/mL]) of selected compounds with respect to further microorganisms

| | | | | | | |
|---|---|---|---|---|---|---|
| Candida albicans ATCC 10231 | 15 | *120 | 15 | *60 | 30 | >60 |
| Aspergillus niger ATCC 6275 | *60 | >60 | 30 | >120 | >60 | >60 |
| Epidermophyton floccosum DSM 10709 | 15 | >60 | 15 | 60 | 15 | *60 |
| Trichophyton mentagrophytes ATCC 9533 | 15 | >60 | *7.5 | >120 | >60 | >60 |

*significant inhibition of growth, but not complete inhibition

Example 3

Determination of the Bactericidal Activity of Selected Compounds

Test Method:

Nutrient Medium:
Casein-soybean flour-peptone broth for preparation of pre-cultures of test bacteria Examples of Test Organisms:
Staphylococcus aureus ATCC 6538
Escherichia coli ATCC 10536
Salmonella choleraesuis ATCC 10708

Procedure:
The test substances are dissolved in dimethyl sulfoxide (DMSO) and tested in a concentration of 120 µg/ml.
Bacteria are incubated overnight in CASO broth and adjusted to an organism count of 1–5×10⁵ CFU/ml using 0.85% sodium chloride solution.
The test substances are pre-pipetted into microtitre plates in amounts of 8 µl per well.
The adjusted test organism suspensions are added in amounts of 192 µl per well to the test substances and mixed. After defined contact times, the test batches are mixed, an aliquot is withdrawn and diluted in several steps in a dilution series of 1:10 in a suitable inactivation medium.
The test plates are incubated for 24 hours at 37° C.
After incubation, the growth is determined on the basis of the turbidity of the test batches (optical density) at 620 nm in a microplate reader.
On the basis of the number of growth-exhibiting steps in the dilution series, the reduction in the test organism concentration is determined in powers of ten (log value).
One microtitre plate is used for each test organism.
All the substances are tested in duplicate.

TABLE 9

Logarithmic reduction in organism count after contact for 30 minutes at a substance concentration of 120 µg/mL

| | Microorganism | | |
|---|---|---|---|
| Compound of formula | S. choleraesuis ATCC 10708 | E. coli NCTC 8196 | S. aureus ATCC 6538 |
| (12) | <1 | <1 | 1–2 |
| (37) | <1 | <1 | 1–2 |
| (44) | <1 | <1 | 1–2 |
| (60) | <1 | <1 | <1 |
| (68) | <1 | <1 | ≦1 |
| (21) | <1 | <1 | 1–2 |
| (45) | <1 | <1 | 1–2 |
| (69) | ≦1 | <1 | 1–2 |
| (77) | <1 | <1 | >3 |
| (22) | <1 | <1 | 1–2 |
| (30) | ≦1 | <1 | ≦1 |
| (46) | <1 | <1 | ≦1 |

TABLE 9-continued

Logarithmic reduction in organism count after contact for 30 minutes at a substance concentration of 120 µg/mL

| | Microorganism | | |
|---|---|---|---|
| Compound of formula | S. choleraesuis ATCC 10708 | E. coli NCTC 8196 | S. aureus ATCC 6538 |
| (54) | ≦1 | ≦1 | 2–3 |
| (70) | <1 | ≦1 | ≦1 |
| (78) | <1 | ≦1 | >3 |
| (7) | <1 | ≦1 | 2 |
| (23) | <1 | <1 | 3 |
| (47) | <1 | <1 | 1 |
| (63) | <1 | ≦1 | <1 |
| (71) | <1 | <1 | 2 |
| (24) | <1 | ≦1 | 2 |
| (32) | ≦1 | <1 | <1 |
| (48) | <1 | <1 | 1 |
| (57) | <1 | <1 | 1 |
| (9) | <1 | <1 | <1 |
| (33) | <1 | <1 | <1 |
| (57) | <1 | <1 | <1 |
| (65) | <1 | <1 | 3 |
| (10) | <1 | <1 | 1–2 |
| (18) | <1 | <1 | 1 |
| (34) | <1 | <1 | <1 |
| (42) | <1 | ≦1 | 2 |
| (58) | ≦1 | ≦1 | 1 |
| (11) | <1 | ≦1 | 1–2 |
| (19) | <1 | ≦1 | 2–3 |
| (35) | <1 | <1 | <1 |
| (43) | <1 | <1 | 3 |
| (83) | <1 | ≦1 | 2 |
| (92) | ≦1 | <1 | >3 |
| (93) | <1 | ≦1 | 2 |
| (89) | ≦1 | ≦1 | 2 |
| (90) | <1 | <1 | 2 |
| (98) | 2–3 | 1–2 | 1 |
| (99) | <1 | ≦1 | 2 |

The invention claimed is:
1. A method for the antimicrobial treatment, deodorisation and disinfection of the skin, mucosa and hair, which comprises applying an antimicrobially effective amount of a compound of the formula (1) thereto

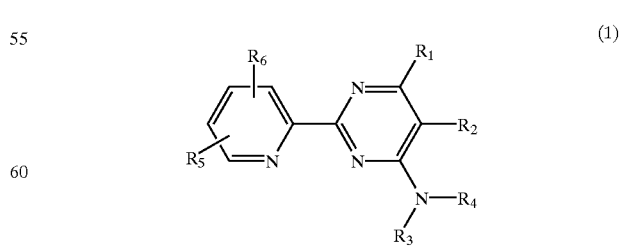

wherein
$R_1$ and $R_2$ are each independently of the other hydrogen; unsubstituted or mono- or poly-halo-substituted $C_1$–$C_{20}$alkyl, $C_1$–$C_{20}$alkoxy, $C_2$–$C_{20}$alkenyl, $C_2$–$C_{20}$alkynyl, $C_3$–$C_{18}$cycloalkyl, $C_3$–$C_7$cycloalkyl-$C_1$–$C_{20}$alkyl; hydroxy; $C_1$–$C_6$alkoxy-$C_1$–$C_{20}$alkyl; carboxy; $C_1$–$C_6$alkyloxycarbonyl; cyano; mono- or di-$C_1$–$C_{20}$alkylamino; $C_1$–$C_6$alkylamino-$C_1$–$C_{20}$alkyl; halogen; phenyl; unsubstituted or $C_1$–$C_5$alkyl-, halo- or hydroxy-substituted phenyl-$C_1$–$C_{20}$alkyl, phenoxy or phenyl-$C_1$–$C_{20}$alkoxy; or $R_1$ and $R_2$ form a polymethylene chain of formula —$(CH_2)_m$— wherein m=2–12;

$R_3$ is unsubstituted $C_7$–$C_{20}$alkyl; or amino-substituted $C_2$–$C_{20}$alkyl or $R_7R_8N$—$C_7$–$C_{20}$alkyl;

$R_4$ is hydrogen; unsubstituted or $C_1$–$C_5$alkyl-, halo- or hydroxy-substituted $C_1$–$C_{20}$alkyl, $C_2$–$C_{20}$alkenyl, $C_2$–$C_{20}$alkynyl, $C_3$–$C_{20}$cycloalkyl, $C_3$–$C_7$cycloalkyl-$C_1$–$C_{20}$alkyl, $C_1$–$C_{20}$alkoxy-$C_1$–$C_6$alkyl or $R_7R_8N$—$C_1$–$C_{20}$alkyl, phenyl, phenyl-$C_1$–$C_{20}$alkyl or phenoxy-$C_1$–$C_{20}$alkyl;

$R_5$ and $R_6$ are hydrogen; and $R_7$ and $R_8$ are each independently of the other $C_1$–$C_{20}$alkyl; $C_3$–$C_{20}$alkenyl; $C_3$–$C_{20}$alkynyl; $C_3$–$C_7$cycloalkyl; $C_3$–$C_{20}$cycloalkyl-$C_1$–$C_4$alkyl; phenyl; or phenyl-$C_1$–$C_4$alkyl.

2. A method according to claim 1, wherein the compound of formula (1) is used for disinfection and deodorisation.

3. A method for the preservation of personel care preparations, which comprises adding a compound of formula (1) to said preparation

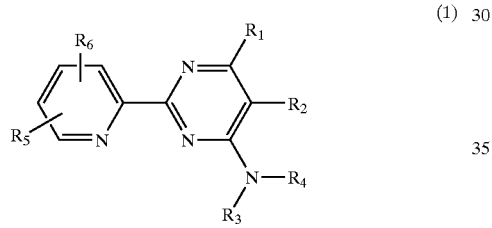

(1)

wherein
$R_1$ and $R_2$ are each independently of the other hydrogen; unsubstituted or mono- or poly-halo-substituted $C_1$–$C_{20}$alkyl, $C_1$–$C_{20}$alkoxy, $C_2$–$C_{20}$alkenyl, $C_2$–$C_{20}$alkynyl, $C_3$–$C_{18}$cycloalkyl, $C_3$–$C_7$cycloalkyl-$C_1$–$C_{20}$alkyl; hydroxy; $C_1$–$C_6$alkoxy-$C_1$–$C_{20}$alkyl; carboxy; $C_1$–$C_6$alkyloxycarbonyl; cyano; mono- or di-$C_1$–$C_{20}$alkylamino; $C_1$–$C_6$alkylamino-$C_1$–$C_{20}$alkyl; halogen; phenyl; unsubstituted or $C_1$–$C_5$alkyl-, halo- or hydroxy-substituted phenyl-$C_1$–$C_{20}$alkyl, phenoxy or phenyl-$C_1$–$C_{20}$alkoxy; or $R_1$ and $R_2$ form a polymethylene chain of formula —$(CH_2)_m$— wherein m=2–12;

$R_3$ is unsubstituted $C_7$–$C_{20}$alkyl; or amino-substituted $C_2$–$C_{20}$alkyl or $R_7R_8N$—$C_7$–$C_{20}$alkyl;

$R_4$ is hydrogen; unsubstituted or $C_1$–$C_5$alkyl-, halo- or hydroxy-substituted $C_1$–$C_{20}$alkyl, $C_2$–$C_{20}$alkenyl, $C_2$–$C_{20}$alkynyl, $C_3$–$C_{20}$cycloalkyl, $C_3$–$C_7$cycloalkyl-$C_1$–$C_{20}$alkyl, $C_1$–$C_{20}$alkoxy-$C_1$–$C_6$alkyl or $R_7R_8N$—$C_1$–$C_{20}$alkyl, phenyl, phenyl-$C_1$–$C_{20}$alkyl or phenoxy-$C_1$–$C_{20}$alkyl;

$R_5$ and $R_6$ are hydrogen; and $R_7$ and $R_8$ are each independently of the other $C_1$–$C_{20}$alkyl; $C_3$–$C_{20}$alkenyl; $C_3$–$C_{20}$alkynyl; $C_3$–$C_7$cycloalkyl; $C_3$–$C_{20}$cycloalkyl-$C_1$–$C_4$alkyl; phenyl; or phenyl-$C_1$–$C_4$alkyl.

4. A method according to claim 3 which comprises adding an antimicrobially effective amount of formula (1) to washing and cleaning formulations.

5. A personal care preparation comprising from 0.01 to 15% by weight, based on the total weight of the composition, of a compound of formula (1)

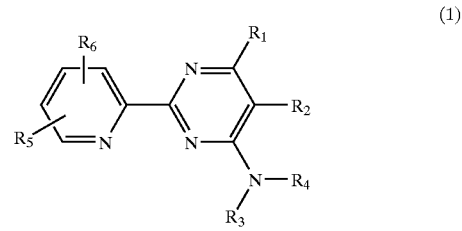

(1)

wherein
$R_1$ and $R_2$ are each independently of the other hydrogen; unsubstituted or mono- or poly-halo-substituted $C_1$–$C_{20}$alkyl, $C_1$–$C_{20}$alkoxy, $C_2$–$C_{20}$alkenyl, $C_2$–$C_{20}$alkynyl, $C_3$–$C_{18}$cycloalkyl, $C_3$–$C_7$cycloalkyl-$C_1$–$C_{20}$alkyl; hydroxy; $C_1$–$C_6$alkoxy-$C_1$–$C_{20}$alkyl; carboxy; $C_1$–$C_6$alkyloxycarbonyl; cyano; mono- or di-$C_1$–$C_{20}$alkylamino; $C_1$–$C_6$alkylamino-$C_1$–$C_{20}$alkyl; halogen; phenyl; unsubstituted or $C_1$–$C_5$alkyl-, halo- or hydroxy-substituted phenyl-$C_1$–$C_{20}$alkyl, phenoxy or phenyl-$C_1$–$C_{20}$alkoxy; or $R_1$ and $R_2$ form a polymethylene chain of formula —$(CH_2)_m$— wherein m=2–12;

$R_3$ is unsubstituted $C_7$–$C_{20}$alkyl; or amino-substituted $C_2$–$C_{20}$alkyl or $R_7R_8N$—$C_7$–$C_{20}$alkyl;

$R_4$ is hydrogen; unsubstituted or $C_1$–$C_5$alkyl-, halo- or hydroxy-substituted $C_1$–$C_{20}$alkyl, $C_2$–$C_{20}$alkenyl, $C_2$–$C_{20}$alkynyl, $C_3$–$C_{20}$cycloalkyl, $C_3$–$C_7$cycloalkyl-$C_1$–$C_{20}$alkyl, $C_1$–$C_{20}$alkoxy-$C_1$–$C_6$alkyl or $R_7R_8N$—$C_1$–$C_{20}$alkyl, phenyl, phenyl-$C_1$–$C_{20}$alkyl or phenoxy-$C_1$–$C_{20}$alkyl;

$R_5$ and $R_6$ are hydrogen; and $R_7$ and $R_8$ are each independently of the other $C_1$–$C_{20}$alkyl; $C_3$–$C_{20}$alkenyl; $C_3$–$C_{20}$alkynyl; $C_3$–$C_7$cycloalkyl; $C_3$–$C_{20}$cycloalkyl-$C_1$–$C_4$alkyl; phenyl; or phenyl-$C_1$–$C_4$alkyl;

and cosmetically tolerable adjuvants.

6. An oral composition comprising from 0.01 to 15% by weight, based on the total weight of the composition, of a compound of formula (1) according to claim 5, and orally tolerable adjuvants.

7. A method according to claim 1, wherein
$R_1$ and $R_2$ are each independently of the other hydrogen, methyl, ethyl, isopropyl, tert-butyl, $CF_3$ or the radical —$(CH_2)_m$—O—$CH_3$;

$R_3$ is unsubstituted or amino-substituted $C_7$–$C_{20}$alkyl or $R_7R_8N$—$C_7$–$C_{20}$alkyl;

$R_4$ is hydrogen; or $C_1$–$C_{20}$alkyl;

$R_5$ and $R_6$ are hydrogen;

$R_7$ and $R_8$ are each independently of the other $C_1$–$C_{20}$alkyl; and m is from 1 to 4.

8. A method according to claim 3, wherein
$R_1$ and $R_2$ are each independently of the other hydrogen, methyl, ethyl, isopropyl, tert-butyl, $CF_3$ or the radical —$(CH_2)_m$—O—$CH_3$;

$R_3$ is unsubstituted or amino-substituted $C_7$–$C_{20}$alkyl or $R_7R_8N$—$C_7$–$C_{20}$alkyl;

$R_4$ is hydrogen; or $C_1$–$C_{20}$alkyl;

$R_5$ and $R_6$ are hydrogen;

$R_7$ and $R_8$ are each independently of the other $C_1$–$C_{20}$alkyl; and m is from 1 to 4.

9. A composition according to claim 5, wherein
$R_1$ and $R_2$ are each independently of the other hydrogen, methyl, ethyl, isopropyl, tert-butyl, $CF_3$ or the radical —$(CH_2)_m$—O—$CH_3$;
$R_3$ is unsubstituted or amino-substituted $C_7$–$C_{20}$alkyl or $R_7R_8N$—$C_7$–$C_{20}$alkyl;
$R_4$ is hydrogen; or $C_1$–$C_{20}$alkyl;
$R_5$ and $R_6$ are hydrogen;
$R_7$ and $R_8$ are each independently of the other $C_1$–$C_{20}$alkyl; and m is from 1 to 4.

10. A composition according to claim 6, wherein
$R_1$ and $R_2$ are each independently of the other hydrogen, methyl, ethyl, isopropyl, tert-butyl, $CF_3$ or the radical —$(CH_2)_m$—O—$CH_3$;
$R_3$ is unsubstituted or amino-substituted $C_7$–$C_{20}$alkyl or $R_7R_8N$—$C_7$–$C_{20}$alkyl;
$R_4$ is hydrogen; or $C_1$–$C_{20}$alkyl;
$R_5$ and $R_6$ are hydrogen;
$R_7$ and $R_8$ are each independently of the other $C_1$–$C_{20}$alkyl; and m is from 1 to 4.

\* \* \* \* \*